(12) United States Patent
Yang et al.

(10) Patent No.: US 12,390,543 B2
(45) Date of Patent: Aug. 19, 2025

(54) RADIANT CATALYTIC IONIZATION DETOXIFICATION SYSTEM AND APPLICATION THEREOF AND RADIANT CATALYTIC IONIZATION DETOXIFICATION METHOD

(71) Applicant: QINGDAO AGRICULTURAL UNIVERSITY, Qingdao (CN)

(72) Inventors: Qingli Yang, Qingdao (CN); Yongchao Ma, Qingdao (CN); Ping Liu, Qingdao (CN); Xiudan Hou, Qingdao (CN); Yinglian Zhu, Qingdao (CN); Jian Ju, Qingdao (CN); Fuguo Xing, Qingdao (CN); Yutao Wang, Qingdao (CN); Zijian Wu, Qingdao (CN)

(73) Assignee: QINGDAO AGRICULTURAL UNIVERSITY, Shandong (CN)

( * ) Notice: Subject to any disclaimer, the term of this patent is extended or adjusted under 35 U.S.C. 154(b) by 0 days.

(21) Appl. No.: 19/080,899

(22) Filed: Mar. 16, 2025

(65) Prior Publication Data
US 2025/0242068 A1      Jul. 31, 2025

Related U.S. Application Data

(63) Continuation of application No. PCT/CN2023/095433, filed on May 22, 2023.

(30) Foreign Application Priority Data

Apr. 21, 2023   (CN) .......................... 202310432102.X

(51) Int. Cl.
 *C02F 1/72*   (2023.01)
 *A23B 2/00*   (2025.01)
 (Continued)

(52) U.S. Cl.
 CPC .............. *A61L 2/088* (2013.01); *A23B 2/001* (2025.01); *A23B 2/503* (2025.01); *A23B 2/53* (2025.01);
 (Continued)

(58) Field of Classification Search
 CPC ... A61L 2/088; A61L 2/10; A61L 2/14; A61L 2202/11; A61L 2202/122; A61L 2202/123;
 (Continued)

(56) References Cited

U.S. PATENT DOCUMENTS 6,309,611 B1 *  10/2001  Tabatabaie-Raissi .... B01J 35/30
                                                          422/186

FOREIGN PATENT DOCUMENTS

CN      102679488 A  *   9/2012
CN      102730906 A       10/2012
 (Continued)

OTHER PUBLICATIONS

JIN Zhiqiang et al, "Synergistric effects of microwave, ultraviolet and ozone combination on mold spores and aflatoxin" Journal of Northwest A&F University (Nat. Sci. Ed.), vol. 46, No. 4, pp. 147-154 (Jan. 10, 2018).

*Primary Examiner* — Regina M Yoo
(74) *Attorney, Agent, or Firm* — SZDC Law PC

(57) ABSTRACT

Disclosed is a radiant catalytic ionization detoxification system including a gas-liquid mixer configured to gas-liquid mix air carrying radiant catalytic ionized Reactive Oxygen Species with liquid material to be detoxified, and a reaction tube configured to circulate the mixed gas-liquid mixture. The detoxification system of the present disclosure is applicable to water sterilization or aflatoxin removal in edible oils. The radiant catalytic ionization chamber in the system can provide the system with air containing Reactive Oxygen
(Continued)

Species, wherein mesh panels coated with photocatalytic materials are configured inside the chamber body, which configuration not only increases the photocatalytic material content per unit volume, but also expands the light-exposed surface area due to uniform distribution of the photocatalytic materials on the mesh panels. The system uses a U-shaped tube as the reaction tube, and the length of the reaction tube can be freely designed according to the practical detoxification requirements.

2 Claims, 9 Drawing Sheets

(51) Int. Cl.
| | | |
|---|---|---|
| *A23B 2/50* | (2025.01) | |
| *A23B 2/53* | (2025.01) | |
| *A23B 20/30* | (2025.01) | |
| *A61L 2/08* | (2006.01) | |
| *A61L 2/10* | (2006.01) | |
| *A61L 2/14* | (2006.01) | |
| *B01J 23/888* | (2006.01) | |
| *B01J 35/39* | (2024.01) | |
| *B01J 37/04* | (2006.01) | |
| *B01J 37/06* | (2006.01) | |
| *B01J 37/08* | (2006.01) | |
| *B01J 37/34* | (2006.01) | |
| *C01G 49/00* | (2006.01) | |
| *C02F 1/32* | (2023.01) | |

(52) U.S. Cl.
CPC ............... *A23B 20/30* (2025.01); *A61L 2/10* (2013.01); *A61L 2/14* (2013.01); *B01J 23/888* (2013.01); *B01J 35/39* (2024.01); *B01J 37/04* (2013.01); *B01J 37/06* (2013.01); *B01J 37/08* (2013.01); *B01J 37/343* (2013.01); *C01G 49/0018* (2013.01); *C02F 1/325* (2013.01); *C02F 1/725* (2013.01); *A61L 2202/11* (2013.01); *A61L 2202/122* (2013.01); *A61L 2202/123* (2013.01); *C01P 2002/72* (2013.01); *C01P 2002/82* (2013.01); *C01P 2002/84* (2013.01); *C01P 2004/03* (2013.01); *C01P 2004/04* (2013.01); *C02F 2305/10* (2013.01)

(58) Field of Classification Search
CPC ........... A23B 2/001; A23B 2/503; A23B 2/53; A23B 20/30; B01J 23/888; B01J 35/39; B01J 37/04; B01J 37/06; B01J 37/08; B01J 37/343; C01G 49/0018; C02F 1/325; C02F 1/725; C02F 2305/10; C01P 2002/72; C01P 2002/82; C01P 2002/84; C01P 2004/03; C01P 2004/04
See application file for complete search history.

(56) References Cited

FOREIGN PATENT DOCUMENTS

| | | | | |
|---|---|---|---|---|
| CN | 105293673 | A | 2/2016 | |
| CN | 105862973 | A * | 8/2016 | ............ B01D 46/30 |
| CN | 207210021 | U | 4/2018 | |
| CN | 208603779 | U | 3/2019 | |
| CN | 109569311 | A | 4/2019 | |
| CN | 111606409 | A | 9/2020 | |
| CN | 112517068 | A | 3/2021 | |
| CN | 114772678 | A | 7/2022 | |
| DE | 19953110 | A | 5/2001 | |
| WO | WO-9817390 | A2 * | 4/1998 | ........... B01D 53/885 |

* cited by examiner

RADIANT CATALYTIC IONIZATION DETOXIFICATION SYSTEM AND APPLICATION THEREOF AND RADIANT CATALYTIC IONIZATION DETOXIFICATION METHOD This application is a Continuation Application of PCT/CN2023/095433, filed on May 22, 2023, which claims priority to Chinese Patent Application No. CN 202310432102.X, filed on Apr. 21, 2023, which is incorporated by reference for all purposes as if fully set forth herein.

TECHNICAL FIELD

The present disclosure relates to technology field of radiant catalytic ionization device, and in particular to, radiant catalytic ionization detoxification system and application thereof and radiant catalytic ionization detoxification method.

BACKGROUND

Radiant catalytic ionized Reactive Oxygen Species are obtained by Radiant Catalytic Ionization (RCI). The Radiant Catalytic Ionization (RCI) is an emerging biocidal detoxification technology that can be used without restriction in human, animal and plant environments as it does not produce potentially hazardous by-products such as ozone, formaldehyde or carbon monoxide. The core of this technology is the photocatalytic effect, i.e., the absorption of light energy with the help of photocatalytic materials generates electron ($e^-$) and hole ($h^+$) pairs, which are converted into reactive oxygen species (ROS) with strong oxidising power and participate in the redox reaction of organic matter. When this technology is used for detoxification and sterilization in prior art, it is carried out under experiment laboratory conditions, and the liquid needs to be in direct contact with the photocatalytic material during the experiments, which poses certain food safety risks. Meanwhile, there is no suitable device to complete treatments of detoxification and sterilization of a large amount of liquid materials under production conditions.

Photocatalytic materials are crucial for radiant catalytic ionization technology, different photocatalytic materials have different efficiency in generating Reactive Oxygen Species, and at present, there are fewer types of photocatalytic materials available, and the more conventional ones are $TiO_2$, ZnO, and so on.

SUMMARY

Regarding to the problems existing in the prior art, the present disclosure proposes a radiant catalytic ionization detoxification system, includes a gas-liquid mixer configured to gas-liquid mix air carrying radiant catalytic ionized Reactive Oxygen Species with liquid material to be detoxified, and a reaction tube configured to circulate the mixed gas-liquid mixture.

Based on the above solution, the reaction tube includes a plurality of U-shaped tubes, and a connecting tube configured to connect the U-shaped tubes; an air supplement tube is detachably connected at a distal end of a straight tube section of the U-shaped tubes, the air supplement tube being configured to introduce air carrying radiant catalytic ionized Reactive Oxygen Species into the U-shaped tubes; a plurality of air supplement holes are disposed on a wall of the air supplement tube.

Based on the above solution, a plurality of fins are disposed on the air supplement tube.

Based on the above solution, the air carrying radiant catalytic ionized Reactive Oxygen Species are provided by a radiant catalytic ionization chamber; the radiant catalytic ionization chamber includes a chamber body, a plurality of mesh panels disposed in the chamber body and a lamp tube configured to provide a radiant light source; a photocatalytic material which produces Reactive Oxygen Species upon light irradiation is coated on the mesh panels.

Based on the above solution, a fixing frame is further disposed in the chamber body, the fixing frame being configured to fix the mesh panels and the lamp tube; a fixing hole configured to fix the lamp tube, and a fixing rod configured to fix the mesh panels are disposed on the fixing frame; a mounting hole configured to be passed through by the lamp tube, and a fixing hole configured to be passed through by the fixing rod are disposed on the mesh panels.

Based on the above solution, the photocatalytic material is $FeWO_4$-rGO composite material.

The present disclosure further provides a method for preparing $FeWO_4$-rGO composite material. Specifically, the method consists of the following steps:

(1) Preparation of $FeWO_4$

Firstly dissolving 5 mmol $FeCl_3 \cdot 6H_2O$ and 5 mmol $Na_2WO_4 \cdot 2H_2O$ respectively into 25 ml distilled water. Then, adding ascorbic acid into FeCl3 solution during continuous stirring for complete dissolution. Next, slowly adding $Na_2WO_4$ solution into the above mixture. after further stirring for 30 min, adding the mixture into 100 mL autoclave (the autoclave was only used as a reaction vessel), maintaining the mixture at 150-200° C. for at least 9 h. Then naturally cooling down the autoclave to room temperature. Collecting a resulting precipitate by centrifugation, and washing several times with distilled water and anhydrous ethanol, and drying in air at 80° C. for 6 h.

wherein: the molar ratio of $Fe^{3+}$: ascorbic acid is: 5:0.2-5:1;

(2) Preparation of $FeWO_4$-rGO Composite Material

Firstly adding 2 g $FeWO_4$ into 300 mL ethanol and ultrasonicating (ultrasonic condition 300 W) for 30 min. After adding 2 mL APTES into $FeWO_4$ suspension, heating the mixture at 70° C. for 4 h. Subsequently collecting the powder, washing with ethanol for several times, then drying it at 80° C. for overnight. Afterwards, adding 1 g APTES-modified $FeWO_4$ into 60 mL distilled water, and ultrasonic treating (ultrasonic condition 300 W) for 15 min, and then adding 0.05 g rGO. After stirring for 60 min, transferring a resulting suspension into an autoclave, and maintaining it at 180° C. for 12 h. Collecting a resulting product, washing with water, and drying at 80° C. overnight, to obtain $FeWO_4$-rGO.

The above radiant catalytic ionization detoxification system can be used for water sterilization or aflatoxin removal in edible oils.

The present disclosure further provides a radiant catalytic ionization detoxification method, applied to the above-described system, includes a step of generating Reactive Oxygen Species according to radiant catalytic ionization, a step of gas-liquid mixing air carrying radiant catalytic ionized Reactive Oxygen Species with liquid materials to be detoxified, and a step of detoxifying bacteria or aflatoxin in liquid materials by Reactive Oxygen Species.

The detoxification system of the present disclosure can be used for water sterilization or aflatoxin removal in edible oils, The radiant catalytic ionization chamber in the system can provide the system with air containing Reactive Oxygen Species wherein mesh panels coated with photocatalytic materials are disposed inside the chamber body, not only increases the photocatalytic material content per unit volume, but also expands the light-exposed surface area due to uniform distribution of the photocatalytic materials on the mesh panels. The system employs a U-shaped tubes as the reaction tube, and the length of the reaction tube can be freely designed according to the practical detoxification requirements, and the installation is convenient and fast, In order to enhance the detoxification efficiency of the system, the system of the present disclosure uses an air supplement tube to continuously replenish new air carrying radiant catalytic ionized Reactive Oxygen Species. Meanwhile, regarding to the photocatalytic material used in the present disclosure, i. e., the $FeWO_4$-rGO composite material, the material is prepared in a simple method, and the method uses ascorbic acid not only as a reducing agent but also as a structure-directing agent to synthesize the $FeWO_4$ product. And the surface charge modification provides a reasonable method for constructing a $FeWO_4$-rGO nanocomposite photocatalyst with sufficient interfacial contact according to electrostatic self-assembly. The $FeWO_4$-rGO composite material prepared by the method of the present disclosure exhibits a strong photocatalytic performance.

DETAILED DESCRIPTION OF THE EMBODIMENTS

Terms used in the present disclosure, unless otherwise indicated, generally have the meanings commonly understood by those of ordinary skill in the art.

Hereinafter, the present disclosure is described in further detail in connection with specific embodiments and with reference to data. The following embodiments are only for the purpose of exemplifying the present disclosure, and are not intended to limit the scope of the present disclosure in any way.

Embodiment 1

Figure 1:
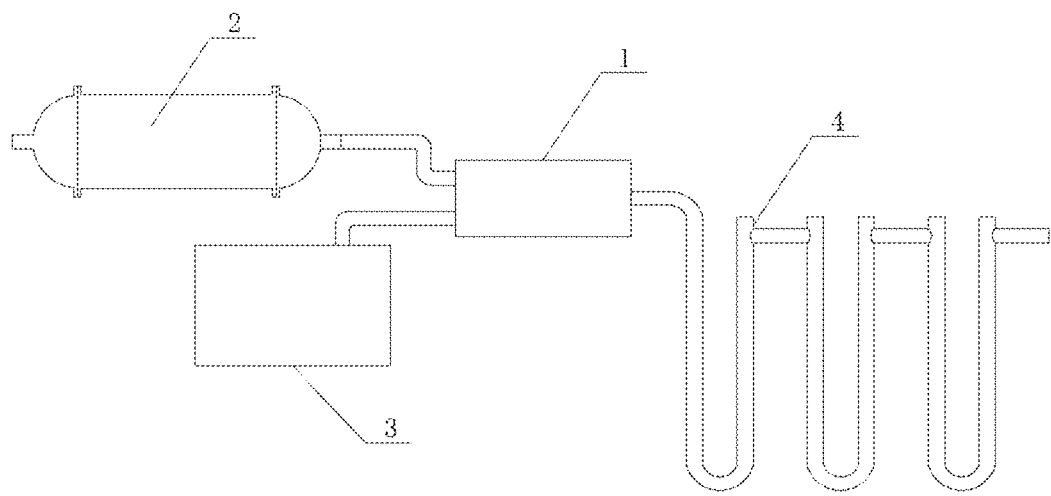
FIG. 1 illustrates a principle schematic diagram of a system described in embodiment 1.

As shown in FIG. 1, the present disclosure provides a radiant catalytic ionization detoxification system, wherein the system includes a gas-liquid mixer 1 configured to gas-liquid mix air carrying radiant catalytic ionized Reactive Oxygen Species with liquid material to be detoxified, and a reaction tube 4 configured to circulate the mixed gas-liquid mixture.

The radiant catalytic ionized Reactive Oxygen Species are obtained by means of Radiant Catalytic Ionization (RCI) technology. The radiant catalytic ionization (RadiantCatalyticIonization, RCI) is an emerging bactericidal detoxification technology that can be used without restriction in human, animal and plant environments as it does not produce potentially dangerous by-products such as ozone, formaldehyde or carbon monoxide. The core of this technology is the photocatalytic effect, i.e., generating electron ($e^-$) and hole ($h^+$) pairs by absorbing light energy with the help of photocatalytic materials, and converting them into Reactive Oxygen Species (ROS) with strong oxidising capacity and participate in the redox reaction of organic substances. There are many photocatalytic materials available, e.g., the photocatalytic materials can use $g-C_3N_4$ and/or FeWO$_4$-rGO composite material, can also use TiO$_2$, Bi$_2$WO$_6$, Upconversionnanoparticles@TiO$_2$, Ag—AgCl/α-Fe$_2$O$_3$ and the like.

The gas-liquid mixer 1 is a device for sufficiently mixing the gas and the liquid. In the mixing process, breaking the gas into small bubbles or micron and nano types of bubbles in the liquid, thereby increasing the contact area between the gas and the liquid, and effectively improving the sufficient redox reaction between Reactive Oxygen Species in the gas and materials to be treated in the liquid.

The liquid material to be detoxified and treated can be aflatoxin-contaminated cooking oil (as well as zearalenone, vomitoxin, etc.), beverage, soya milk, milk, etc., or sewage to be sterilized.

The detoxification system of the present disclosure uses the photocatalytic material and the liquid to be treated without contact to each other to carry out the detoxification treatment, which firstly avoids the secondary contamination of the liquid by the photocatalytic material, and secondly avoids the risk of quality degradation caused by the liquid being directly irradiated by the light (e.g., the light will change the acidity, the peroxide value, the unsaturated fatty acid, etc. of the peanut oil).

In a process wherein Air carrying Reactive Oxygen Species and liquid materials to be detoxified circulates in the reaction tube 4, the Reactive Oxygen Species constantly play redox reaction. However, with the continuous consumption of Reactive Oxygen Species in the air, the oxidation capacity of the gas is gradually reduced. In order to solve this problem, it is necessary to constantly filled with air carrying radiant catalytic ionized Reactive Oxygen Species, in a process of gas-liquid mixtures circulating in the reaction tube 4, and thus achieve a rapid processing effect. When the amount of Reactive Oxygen Species (ROS) in the air carrying Reactive Oxygen Species (ROS) replenished into the liquid materials is sufficient, there is no need to add new Reactive Oxygen Species into the reaction tube 4. But if the air carrying Reactive Oxygen Species (ROS) replenished into the liquid material is insufficient to treat the liquid materials to be detoxified, based on the above mentioned technical solution, it is necessary to continually replenish the air carrying radiant catalytic ionized Reactive Oxygen Species (ROS) into the gas-liquid mixture during circulating the gas-liquid mixture in the reaction tube 4.

Figure 4:
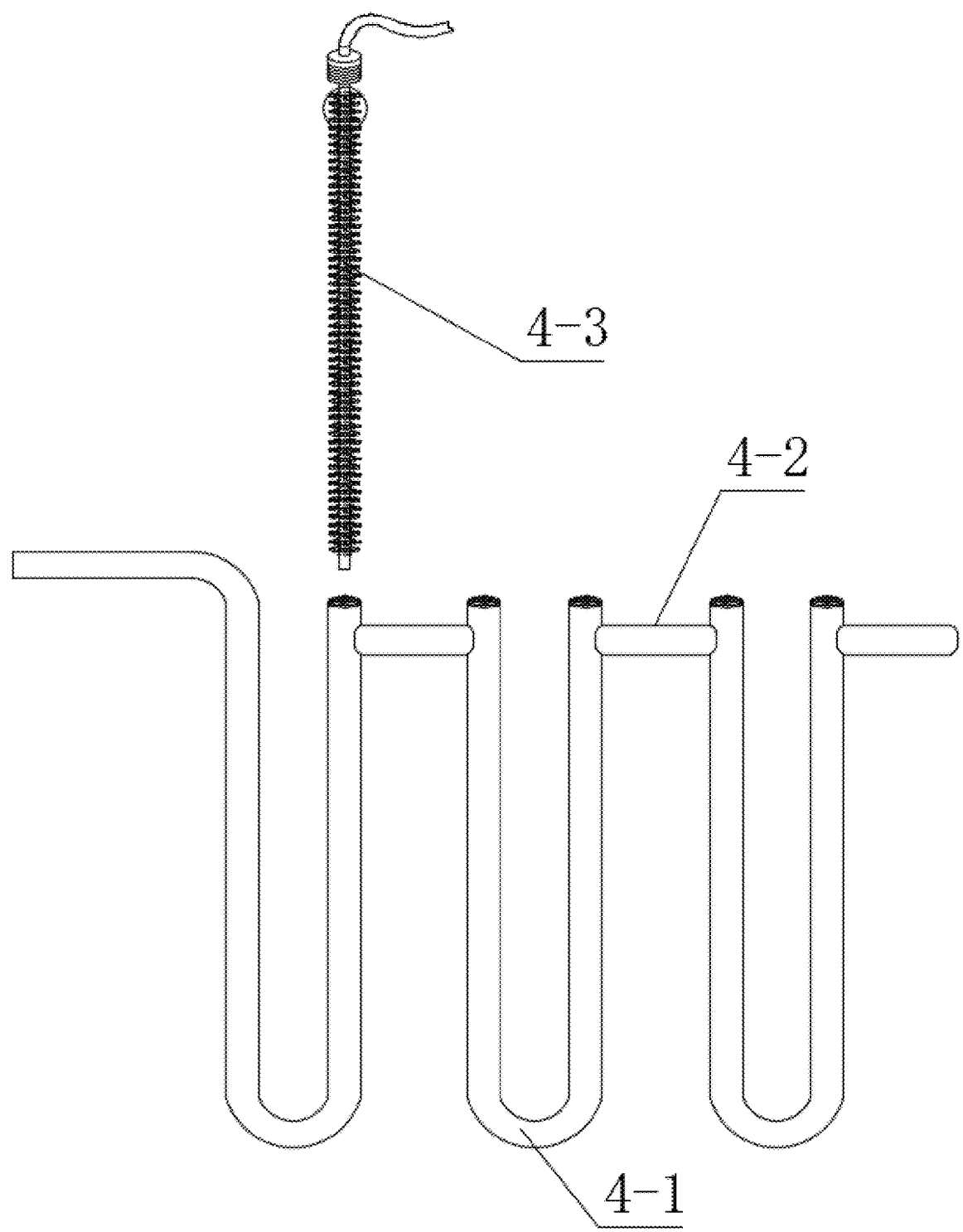
FIG. 4 illustrates a structure schematic diagram of a reaction tube in the detoxification system described in the present disclosure.

As a specific implementation, the present disclosure provides a specific embodiment of the reaction tube 4, as shown in FIG. 4, the reaction tube 4 includes a plurality of U-shaped tubes 4-1 and a connecting tube 4-2 for connecting the U-shaped tubes 4-1; the connecting tubes 4-2 can be connected between the U-shaped tubes 4-1 by means of threaded connection, and in this way, the length of the reaction tubes can be freely designed according to the practical detoxification requirements, and the installation is convenient and fast.

During circulating the mixed materials in the reaction tube 4, the Reactive Oxygen Species in the air are continuously consumed, and the oxidation capacity of the gas gradually decreases, therefore, in order to improve the detoxification efficiency, it is necessary to maintain the content of Reactive Oxygen Species in the mixed materials. And for this purpose, it is necessary to continuously replenish new air carrying radiant catalytic ionized Reactive Oxygen Species. As a specific implementation, as shown in FIG. 4, the present disclosure designs a distal end of a straight tube section of the U-shaped tubes 4-1 as an opening structure that can be opened or closed at any time, so that when it is necessary to replenish the Reactive Oxygen Species gas, the opening is opened, and an air supplement tube 4-3 is inserted into the straight tube section from the opening, and the air carrying radiant catalytic ionized Reactive Oxygen Species are replenished into the U-shaped tubes 4-1 by the air supplement tube 4-3. The air supplement tube 4-3 is detachably connected to a distal end of a straight tube section of U-shaped tubes 4-1. When there is no need to replenish air, the distal end of the straight tube section of the U-shaped tube 4-1 can be blocked with a plug (not shown in the drawings yet). A plurality of air supplement holes 4-31 is disposed on the wall of the air supplement tube 4-3.

Figure 5:
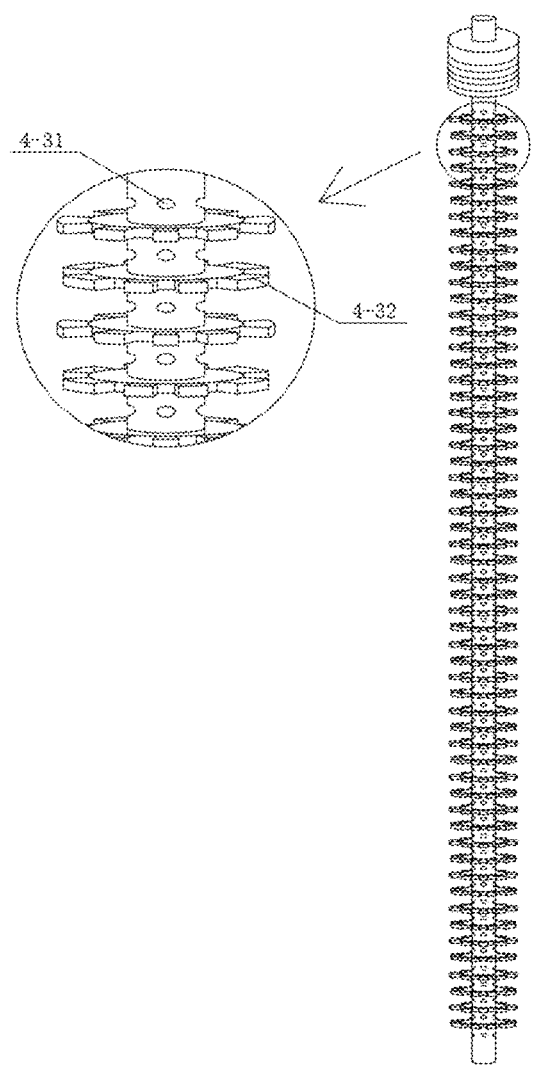
FIG. 5 illustrates a structure schematic diagram and a partially enlarged schematic diagram of an air supplement tube in the detoxification system described in the present disclosure.

In order to improve the mixing degree between the newly replenished gas and the liquid, as shown in FIG. 5, a plurality of fins 4-32 are disposed on the air supplement tube 4-3. The provision of a plurality of fins 4-32 not only can break the newly replenished gas into small bubbles, but also at the same time, can effectively improve the mixing degree between the gas and the liquid.

Figure 2:
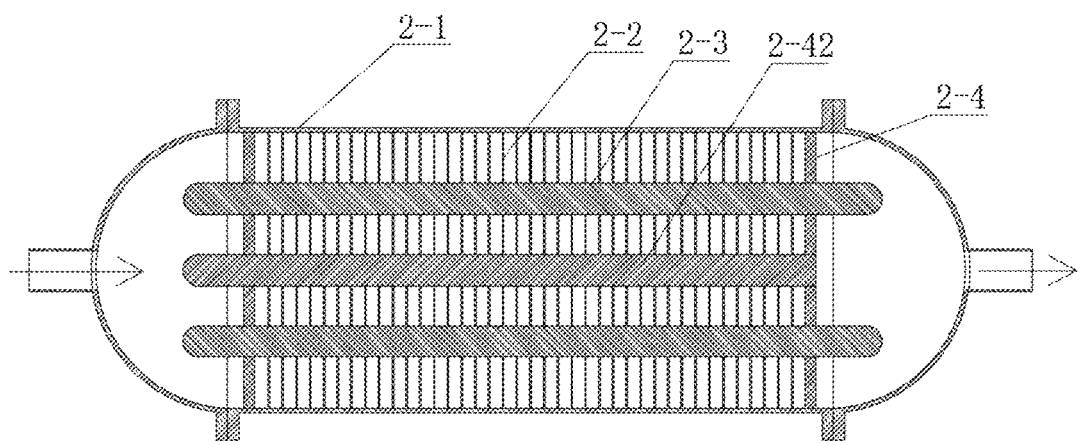
FIG. 2 illustrates a structure schematic diagram of a radiant catalytic ionization chamber in the detoxification system described in the present disclosure.

Regarding to the detoxification system of the present disclosure, the amount of Reactive Oxygen Species carried in the air is crucial to the detoxification effect, in order to improve the concentration of Reactive Oxygen Species carried in the air, the present disclosure provides a specific embodiment. As shown in FIG. 2, the air carrying radiant catalytic ionized Reactive Oxygen Species are provided by an radiant catalytic ionization chamber 2; the radiant catalytic ionization chamber 2 includes a chamber body 2-1, a plurality of mesh panels 2-2 disposed in the chamber body 2-1, and a lamp tube 2-3 for providing a light source for irradiation; the mesh panels 2-2 are attached with photocatalytic material for generating Reactive Oxygen Species upon light irradiation.

A plurality of mesh panels 2-2 coated with photocatalytic materials disposed in the radiant catalytic ionization chamber 2 of the present disclosure could stimulate more Reactive Oxygen Species under irradiation of the lamp tube 2-3; the chamber body 2-1 is open at both ends, with an air inlet at one end and an air outlet at the other end, and the Reactive Oxygen Species are driven by a blower (which is not shown in the drawings yet) to enter from the chamber 2 into a gas-liquid mixer 1, so as to be mixed with the liquid material to be treated. Specifically, the mesh panels 2-2 may use a mesh panel of a light-transmitting material; and a photocatalytic material is attached to the surface of the mesh panels 2-2. Compared with the existing catalytic ionization device, the radiant catalytic ionization chamber 2 of the present disclosure uses the mesh panels 2-2 coated with the photocatalytic materials, instead of setting the photocatalytic material on a flat plate. Therefore, the present disclosure not only increases the photocatalytic material content per unit volume, but also increases the area of light illumination at the same time due to the photocatalytic material being uniformly attached to the surface of the mesh panels. At the same time, the mesh structure of the mesh panels 2-2 is more loaded with the photocatalytic material, under a premise that it meets the need of gas circulation and facilitates the circulating air to pass through mesh panels and to take away the Reactive Oxygen Species generated by the irradiation of the photocatalytic material on the mesh panel, so as to provide the system with sufficient Reactive Oxygen Species. As a specific embodiment, the mesh panels 2-2 use a light transmissive acrylic, PC or PVC rigid sheet covered with air permeable holes, and photocatalytic materials are attached to the mesh panels 2-2.

Figure 3:
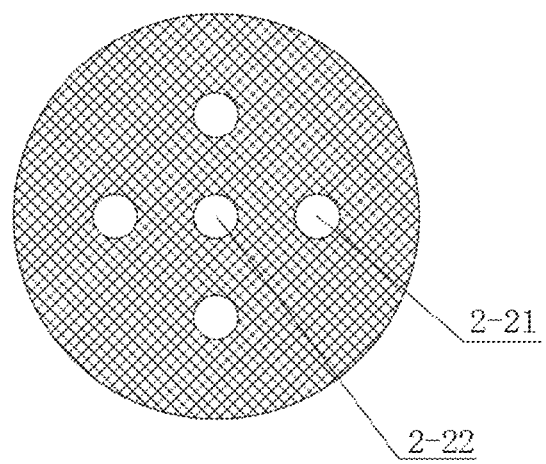
FIG. 3 illustrates a structure schematic diagram of mesh panels in the detoxification system described in the present disclosure.

As a specific application solution, as shown in FIG. 2, in the chamber body 2-1, a fixing frame 2-4 is further provided for fixing the mesh panels 2-2 and the lamp tube 2-3; on the fixing frame 2-4, fixing holes 2-41 are provided for fixing the lamp tube 2-3, and a fixing rod 2-42 is provided for fixing the mesh panels 2-2. And as shown in FIG. 3, on the mesh panels 2-2, a mounting hole 2-21 is provided for the lamp tube 2-3 to pass through, and a fixing hole 2-22 is provided for the fixing rods 2-42 to pass through. In this way, it is possible to assemble the mesh panels 2-2, the lamp tube 2-3 and the fixing frame 2-4 outside the chamber body 2-1 in advance, to insert them into the chamber body 2-1 after assembly, and to fix the fixing frame 2-4 inside the chamber body 2-1 (the four legs of the fixing frame 2-4 are fixed to the inner wall of the chamber body 2-1). Only one embodiment of the position and number of a mounting hole 2-21 and a fixing hole 2-22 is given in FIG. 3. And when used, the position and number of the mounting hole 2-21 and the fixing hole 2-22 can be freely set according to requirements.

Figure 6:
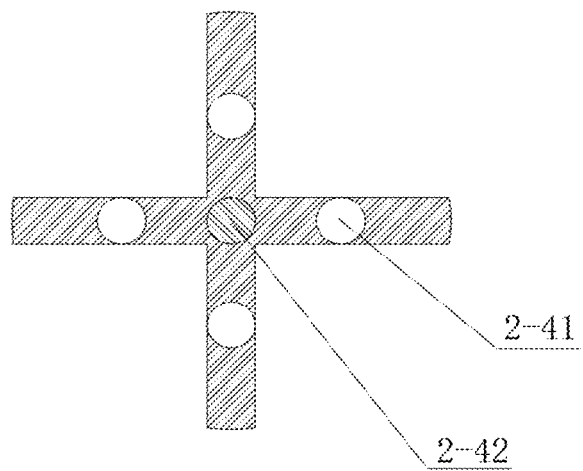
FIG. 6 illustrates a structure schematic diagram of a fixing frame in the detoxification system described in the present disclosure.

The structure of the fixing frame 2-4 is shown in FIG. 6, because the chamber body 2-1 is ventilated therein when in use, in order to increase the stability of the mesh panels 2-2 and the lamp tube 2-3, as shown in FIG. 2, a fixing frame is added onto the other side of the plurality of mesh panels (the left side in the FIG. 2), and the middle of this fixing frame consists of a round hole instead of the fixing rod, the round hole being used for insertion of the fixing rod 2-42, which will not be described herein.

The specific type of the lamp tube 2-3 is not particularly limited, as long as it is capable of irradiating the catalytic semiconductor material to produce Reactive Oxygen Species, such as ordinary fluorescent lamp tubes or lamp tubes that produce special wavelengths of light, such as in embodiment 3 wherein a 300 W xenon lamp and an optical cut-off filter are used.

When in use, the lamp tube 2-3 in the radiant catalytic ionization chamber 2 are turned on for irradiation catalysis, and a pump is used to pump the material to be treated in the material-liquid tank 3 into the gas-liquid mixer 1. At the same time, a blower is used to replenish the Reactive Oxygen Species produced by the radiant catalytic ionization chamber 2 into the gas-liquid mixer 1 to mix it with the liquid materials, and the mixed materials are pumped by the pump into the reaction tube 4, so as to be detoxified. Inside the reaction tube 4, the oxidising capacity of the gas gradually decreases, so in order to improve the detoxification efficiency, the air supplement tube 4-3 is used to replenish gas to the reaction tube 4.

Embodiment 2

Based on the detoxification system in embodiment 1, the present embodiment 2 provides a photocatalytic material-$FeWO_4$-rGO composite material that can be used in the detoxification system, the $FeWO_4$-rGO composite material being prepared by the following methods:

(1) Preparation of $FeWO_4$

Firstly dissolving 5 mmol $FeCl_3 \cdot 6H_2O$ and 5 mmol $Na_2WO_4 \cdot 2H_2O$ respectively into 25 ml distilled water. Then, adding 0.5 mmol ascorbic acid into $FeCl_3$ solution under continuous stirring for complete dissolution. Next, slowly adding $Na_2WO_4$ solution into the above mixture. After further stirring for 30 min, adding the mixture into 100 mL autoclave (the autoclave in this embodiment 2 was only used as a reaction vessel), and maintaining at 180° C. for 12 h. Then naturally cooling down the autoclave to room temperature. Collecting a resulting precipitate by centrifugation, and washing with distilled water and anhydrous ethanol several times, and drying in air at 80° C. for 6 h.

(2) Preparation of $FeWO_4$-rGO Composite Material

Firstly adding 2 g $FeWO_4$ into 300 mL ethanol, and ultrasonic treating a mixture of the 2 g $FeWO_4$ and 300 mL ethanol (ultrasonic condition 300 W) for 30 min. After adding 2 m LAPTES into $FeWO_4$ suspension, heating the mixture at 70° C. for 4 h. Subsequently collecting the powder, washing with ethanol for several times, then drying it at 80° C. for overnight. Afterwards, adding 1 g APTES-modified $FeWO_4$ into 60 mL distilled water, and ultrasonic treating (ultrasonic condition 300 W) for 15 min, and then adding 0.05 g rGO. After stirring for 60 min, transferring a resulting suspension into an autoclave, and maintaining it at 180° C. for 12 h. Collecting a resulting product, washing with water, and drying at 80° C. for overnight, to obtain $FeWO_4$-rGO.

Embodiment 3

In order to compare the superiority of charge modification method, snowflake-like FeWO4 prepared in step (1), $FeWO_4$-rGO-U ($FeWO_4$-rGO-U is a mixture of $FeWO_4$ and rGO milled and mixed directly) and $FeWO_4$-rGO prepared by the above method were compared and tested, respectively.

(1) XRD Test

Figure 7:
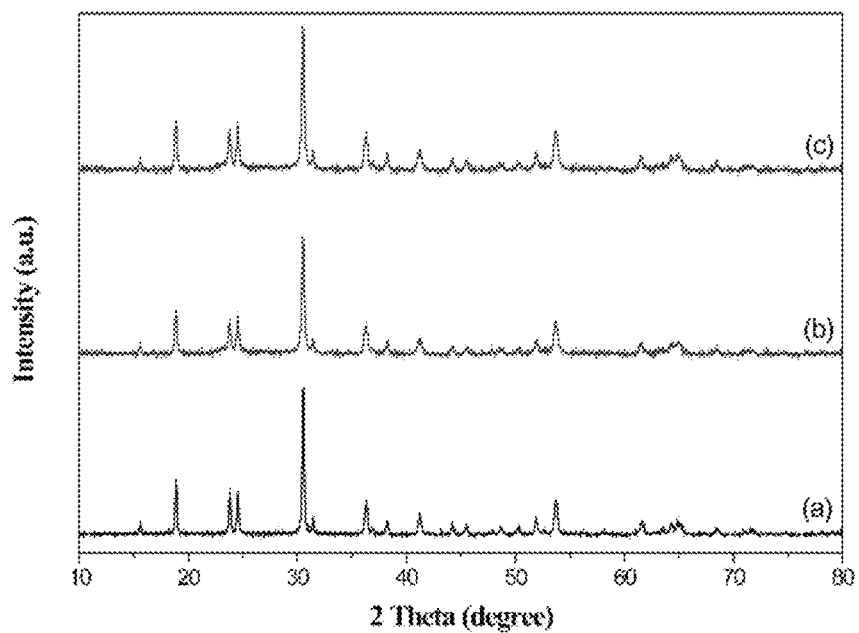
FIG. 7 illustrates a schematic diagram of an XRD pattern of the sample in embodiment 2, wherein, (a) snowflake-like $FeWO_4$, (b) $FeWO_4$-rGO-U, and (c) $FeWO_4$-rGO.

The results are shown in FIG. 7. All diffraction peaks of the product can be attributed to the standard card of $FeWO_4$ (JCPDS No. 46-1446). In addition, no diffraction peaks of rGO were observed.

(2) Raman Spectroscopy Test

Figure 8:
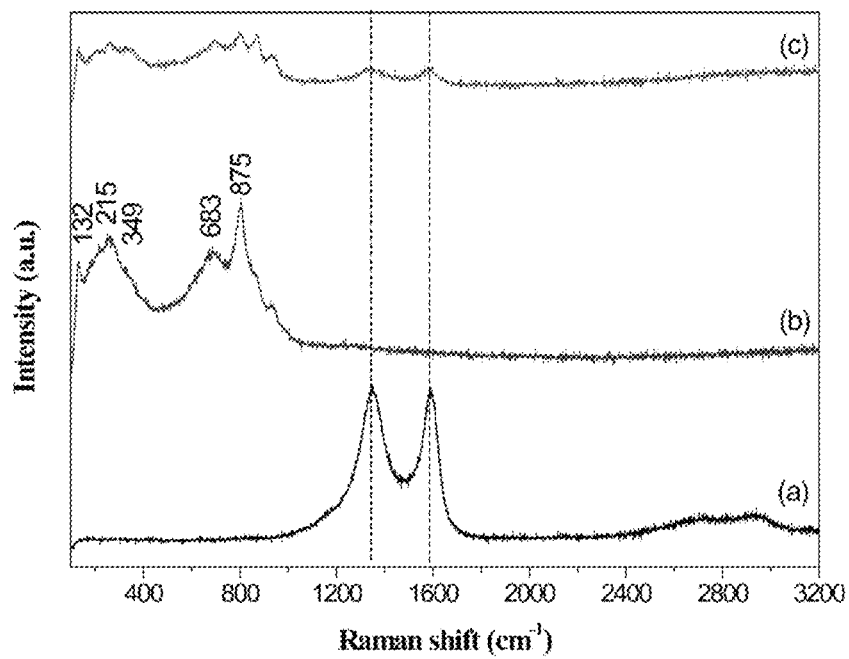
FIG. 8 illustrates a schematic diagram of a Raman spectrum of the sample in embodiment 2, wherein, (a) GO, (b) $FeWO_4$, and (c) $FeWO_4$-rGO.

The results are shown in FIG. 8, and the presence of rGO in the complex was further determined by Raman analysis. As shown in FIG. 8 (a), two main peaks were observed near 1596 and 1346 $cm^{-1}$, which should be attributed to the G band and D band of GO. The peaks at 93, 132, 215, 179, 349, 683 and 875 $cm^{-1}$ correspond to the Raman spectrum of $FeWO_4$, as shown in (b) in FIG. 8. Regarding to the $FeWO_4$-rGO composite material, in addition to the peaks attributed to $FeWO_4$, the G band and D band of rGO are located at 1598 $cm^{-1}$ and 1345 $cm^{-1}$, respectively. This clearly indicates the presence of rGO in the prepared rGO-$FeWO_4$ composites.

(3) UV-Vis Diffuse Reflection

Figure 9:
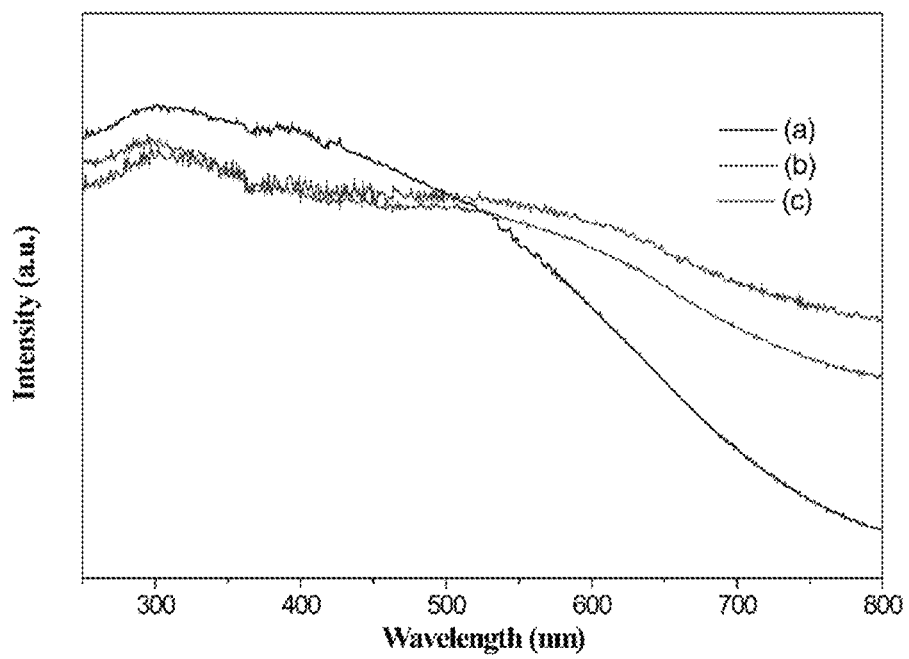
FIG. 9 illustrates a schematic diagram of a UV-vis diffuse reflectance spectrum of samples in embodiment 2, wherein, (a) $FeWO_4$, (b) $FeWO_4$-rGO-U, and (c) $FeWO_4$-rGO.

The results are shown in FIG. 9, the optical properties of the material can be characterized by UV-vis DRS spectrum; and the snowflake-like $FeWO^4$ shows strong absorption in the visible region. Enhanced absorption of visible light in the region between 500 and 800 nm can be clearly observed, by adding rGO. Extension of the light absorption range enables more efficient use of the solar spectrum and enhanced photocatalytic activity. In addition, the background absorption of $FeWO^4$-rGO composite material is significantly enhanced in the visible region.

(4) $N_2$ Adsorption and Desorption

Figure 10:
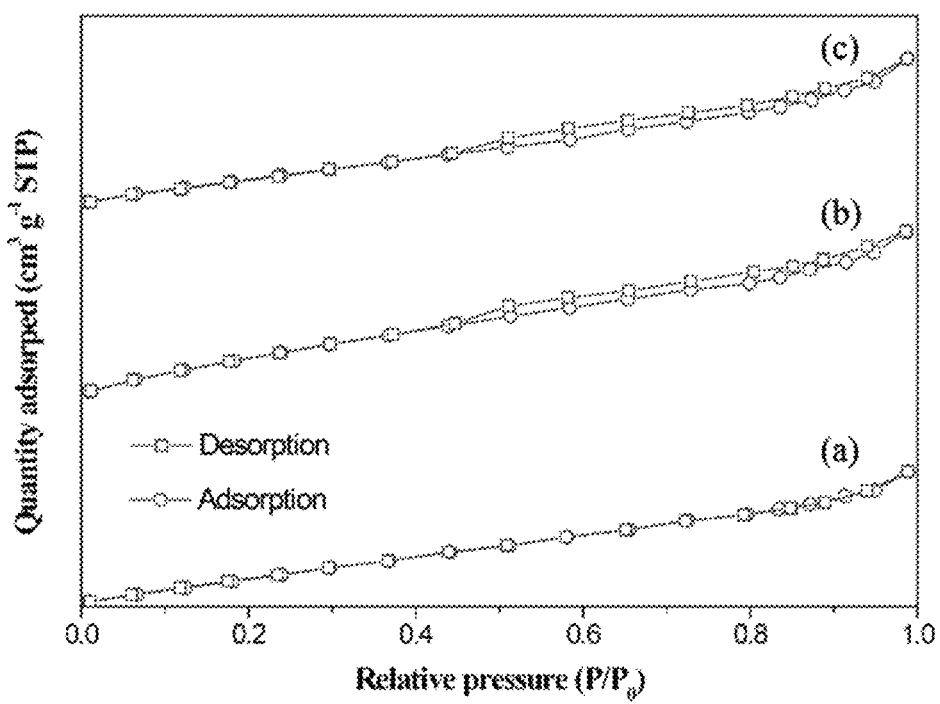
FIG. 10 illustrates a schematic diagram of N2 adsorption and desorption isotherms of the sample in embodiment 2; wherein, (a) snowflake-like $FeWO_4$, (b) $FeWO_4$-rGO-U, and (c) $FeWO_4$-rGO.

The $N_2$ adsorption-desorption isotherms of the prepared products are shown in FIG. 10. The specific surface areas of FeWO$_4$-rGO, FeWO$_4$-rGO-U and pure snowflake-like FeWO$_4$ were 49.18, 47.03 and 45.80 cm$^3$g$^{-1}$, respectively, with no significant difference in values.

(5) SEM Test and TEM Test

Figure 11:
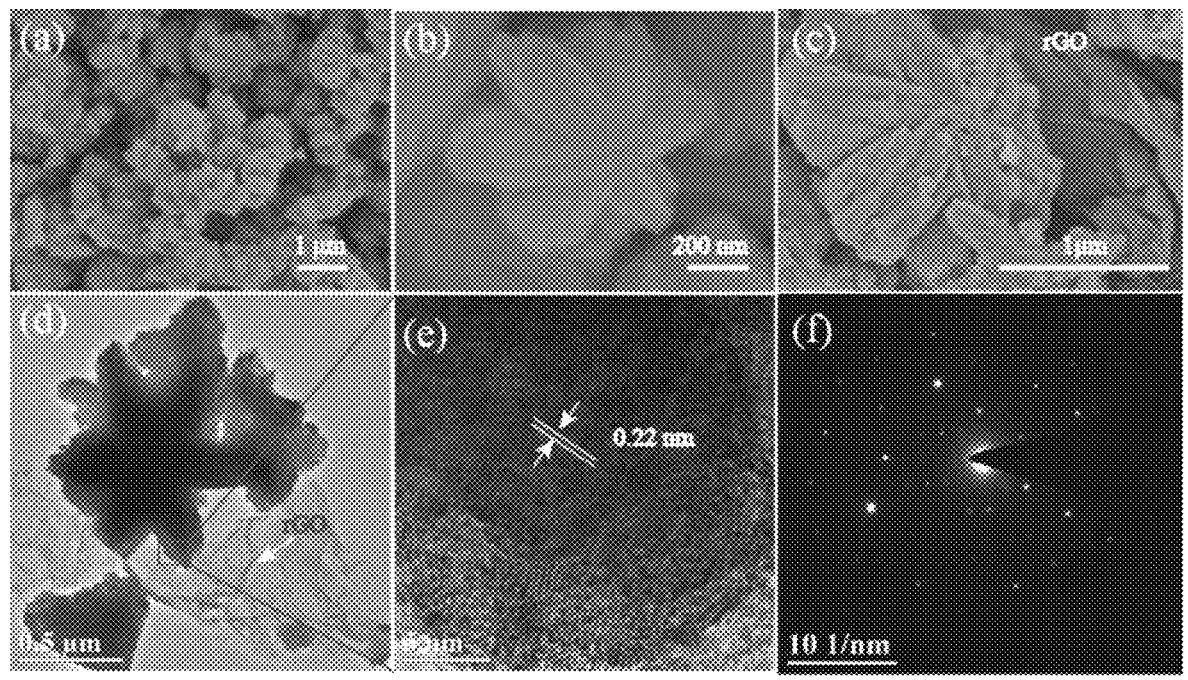
FIG. 11 illustrates scanning electron microscopy (SEM) and transmission electron microscopy images of the samples in embodiment 2; (a, b) snowflake-like $FeWO_4$, (c) SEM images of $FeWO_4$-rGO composite material, (d) (e) HRTEM, and (f) corresponding SAED of $FeWO_4$-rGO composite materials.

The results are shown in FIG. 11, wherein the morphology and structure of snowflake-like FeWO$_4$ and FeWO$_4$-rGO composite materials were investigated by SEM and TEM. As shown in (a) of FIG. 11, FeWO$_4$ consists of uniform snowflake-like microcrystals with a diameter of about 1 μm. High-magnification SEM shows that each snowflake-like FeWO$_4$ with approximate sixfold symmetry consists of nanorods assembled in specific directions (b in FIG. 11). As for the FeWO$_4$-rGO materials (c-d in FIG. 11), FeWO$_4$ is wrapped by rGO nanosheets, which implies the possibility of full contact and effective interfacial interactions between FeWO$_4$ and rGO. The TEM of the FeWO$_4$-rGO composite material is shown in FIG. 11, (d). The FeWO$_4$ assemblies are deposited on the surface of the rGO sheets. The sample shows some folds at the edges of both the rGO sheet and the sandwich sheet, providing more adsorption active sites. A well-defined lattice stripe with a spacing of 0.22 nm, which corresponds to the (020) plane of FeWO$_4$, is shown in (e) of FIG. 11. In addition, selected area electron diffraction (SAED) shows well-defined rings, which confirms the polycrystalline nature of the sample.

Figure 12:
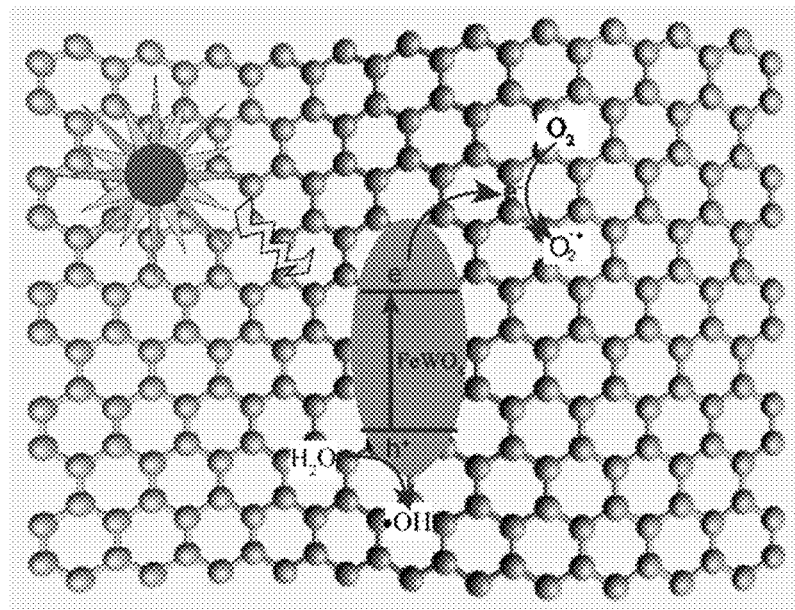
FIG. 12 illustrates a schematic reaction mechanism diagram of the photocatalytic redox reaction on the $FeWO_4$-rGO composite photocatalyst under visible light irradiation.

As shown in FIG. 12, under visible light irradiation, electrons in the valence band (VB) are excited into the conduction band (CB), leaving holes in the VB and generating electron-hole pairs in FeWO$_4$. Photogenerated electrons (e$^-$) are then transferred from the FeWO$_4$ microstructure to the rGO sheet and further react with O$_2$ to produce highly reactive free radicals (O$^{2-}$). Holes in the VB of FeWO$_4$ react with water to form reactive OH$^-$. These free radicals are capable of attacking fungal toxins and abrogating the fungal toxins according to photocatalytic redox reactions. On the other hand, the surface charge modification provides a rational method for constructing FeWO$_4$-rGO nanocomposite photocatalysts with sufficient interfacial contacts according to electrostatic self-assembly, as compared to FeWO$_4$-GO-U composite material. All of the above factors contribute to the improvement of the separation efficiency of electron-hole pairs, which significantly enhances the photoactivity of the FeWO$_4$-rGO composite material.

Morphological Changes of the Generated FeWO$_4$ Under Different Temperature Conditions Firstly dissolving 5 mmol FeCl$_3$·6H$_2$O and 5 mmol Na$_2$WO$_4$·2H$_2$O respectively into 25 ml distilled water. Then, adding 0.5 mmol ascorbic acid into the FeCl$_3$ solution under continuous stirring for complete dissolution. Next, slowly adding Na$_2$WO$_4$ solution into the above mixture. After further stirring for 30 min, the mixture was added into 100 mL autoclave, maintaining it at a certain temperature for 12 h. Then naturally cooling down the autoclave to room temperature. Collecting a resulting precipitate by centrifugation, and washing several times with distilled water and anhydrous ethanol, and drying it in air at 80° C. for 6 h.

Figure 13:
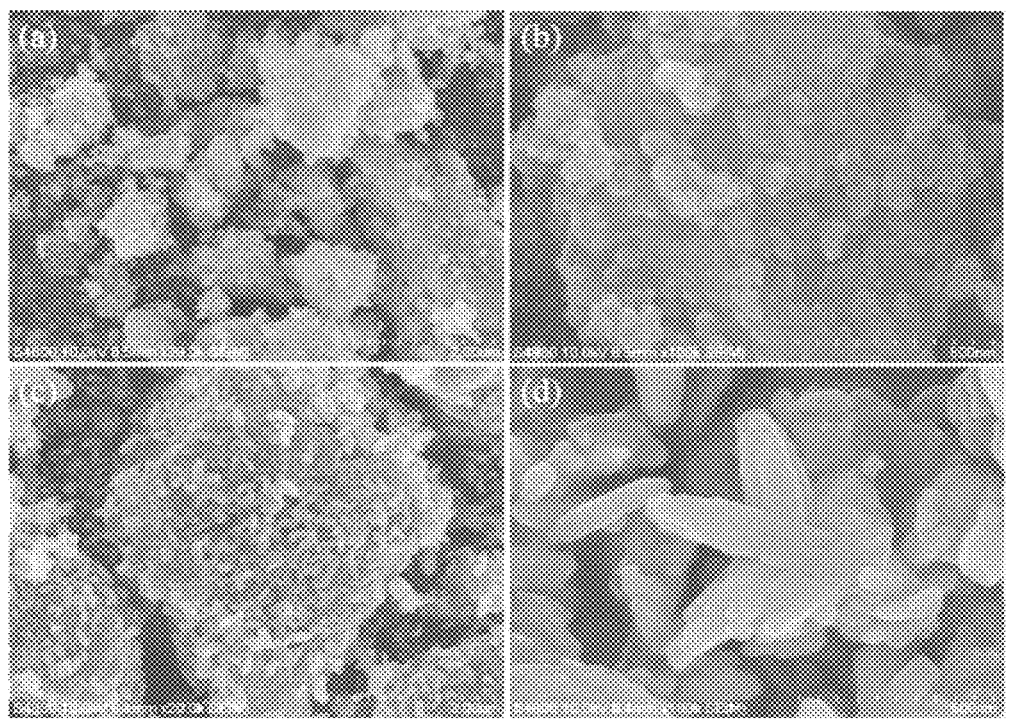
FIG. 13 illustrates SEM images of $FeWO_4$ generated under different temperature conditions; wherein, (a) 120° C., (b) 150° C., (c, d) 200° C.

The results are shown in FIG. 13. FIG. 13 shows the effect of temperature on the morphology of FeWO$_4$ samples. Irregular shapes were observed at 120° C. ((a) in FIG. 13). Upon increasing the temperature to 150° C., the average size of the products was smaller, although the morphology of the products was similar to that of the 120° C. hydrothermal-treated samples. When the temperature was increased to 180° C. ((a) and (b) in FIG. 11), the prepared samples consisted of snowflakes with perfect homogeneity. When the temperature was increased to 200° C., the surface of the nanorods became smoother, although the samples maintained a snowflake-like structure ((c) and (d) in FIG. 13). This result also suggests that the final morphology depends on the formation temperature of FeWO$_4$ crystals.

Morphological Changes of the Generated FeWO$_4$ Under Different Time Conditions

Firstly, dissolving 5 mmol FeCl$_3$·6H$_2$O and 5 mmol Na$_2$WO$_4$·2H$_2$O respectively into 25 ml distilled water. Then, adding 0.5 mmol ascorbic acid into the FeCl3 solution under continuous stirring for complete dissolution. Next, slowly adding Na$_2$WO$_4$ solution into the above mixture. After further stirring for 30 min, adding the mixture into a 100 mL autoclave and maintaining it at 180° C. for a certain period of time. Then naturally cooling the autoclave to room temperature. Collecting a resulting precipitate by centrifugation, and washing it several times with distilled water and anhydrous ethanol, and drying it in air at 80° C. for 6 h.

Figure 14:
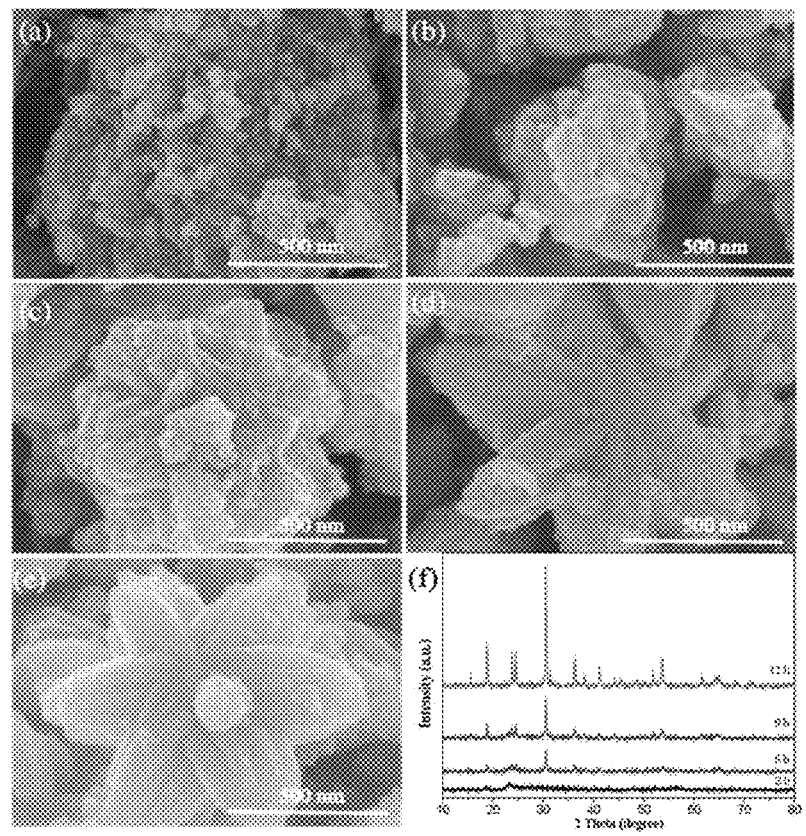
FIG. 14 illustrates SEM patterns and XRD patterns of $FeWO_4$ generated under different time conditions; (a) 0 h, (b) 2 h, (c) 6 h, (d) 9 h, and (e) 12 h. (f) XRD patterns of the prepared samples after hydrothermal treatment at 180° C. for different reaction times.

In order to understand the growth mechanism of snowflake-like FeWO$_4$, SEM of the material prepared at different hydrothermal times is shown in FIG. 14. When the reaction time was lower than 2 h, the products consisted of large ovoid particles ((a) and (b) in FIG. 14). The image of the sample reacted for 6 h is shown in (c) in FIG. 14, indicating the formation of plate-like aggregates. These aggregates were formed from many nanoparticles and nanorods. As the process continues, snowflake-like FeWO$_4$ structures appear after 9 h, showing hexagonal symmetry ((d) in FIG. 14). It should be noted that the nanorods extend outwards from the center of the aggregates in a self-assembled form. As the reaction continued, the irregular particles disappeared and longer nanorods were formed, suggesting that the longer nanorods grew at the expense of smaller particles. After 12 h, the nanoparticles on the snowflake surface of the FeWO$_4$ grew along its axis, to form nanorods ((e) in FIG. 14). These images clearly show the shape evolution process of the obtained product from aggregates built of nanoparticles to snowflake-like structures. XRD patterns of FeWO$_4$ samples prepared at different hydrothermal times are shown in (f) in FIG. 14. The crystalline phase is enhanced with increasing hydrothermal time. All XRD patterns can be easily identified as FeWO$_4$.

Figure 15:
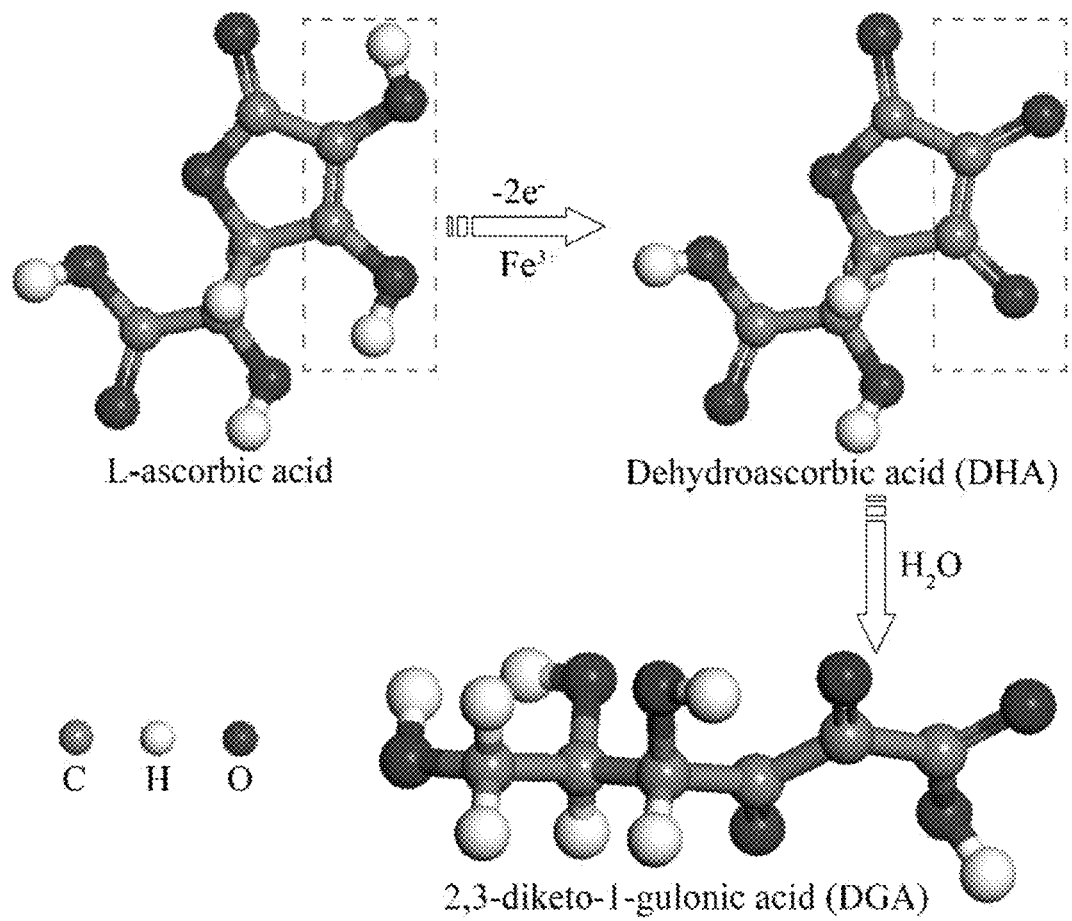
FIG. 15 illustrates a schematic diagram of oxidation process of L-ascorbic acid.
Figure 16:
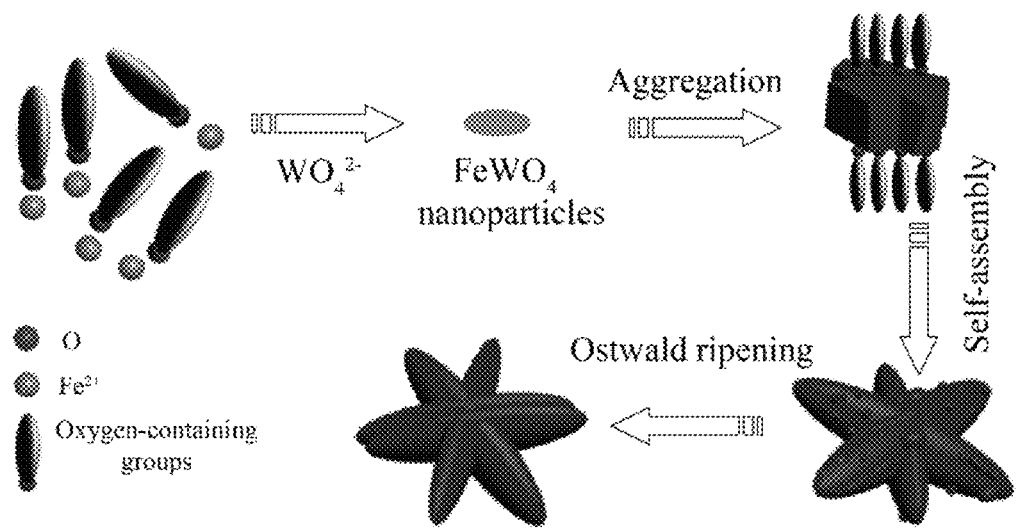
FIG. 16 illustrates a schematic diagram of forming $FeWO_4$ with snowflake-like structure.

Based on the above analysis, the shape evolution process of the snowflake-like microstructures is shown in FIG. 15 and FIG. 16. During this process, oxygen-containing groups (e.g., –OH and C=O) in DHA and DGA strongly tend to coordinate with Fe$^{2+}$ cations and form complexes. As a result, the concentration of free Fe$^{2+}$ cations decreases. The slow formation rate of FeWO$_4$ will lead to a separation of a nucleation step and a growth step. Then WO$_4^{2-}$ reacts with the complexes to form FeWO$_4$ nuclei. DHA and DGA in the reaction system are absorbed by the surface of the FeWO$_4$ nuclei. At the same time, the FeWO$_4$ nuclei tend to aggregate, due to the decrease in the surface energy of the nuclei and the hydrogen interaction between DHA and DGA. In addition, due to the high intrinsic anisotropic nature of FeWO$_4$, the nanoparticles preferred to grow into nanorods by directional attachment. With time prolongation of hydrothermal treatment, snowflake-like microstructures were formed. We can conclude that the formation of graded snowflake-like microstructures is a result of ascorbic acid-induced reduction, formation and aggregation of nanoparticles followed by growth of nanorods and their subsequent self-assembly. According to the reported literature, after modification by APTES, FeWO$_4$ has amine functional groups. Under the effect of electrostatic attraction, FeWO4 was anchored to the surface of negatively charged rGO nanosheets.

Effect of Different Amounts of Ascorbic Acid on Product Morphology

Firstly dissolving 5 mmol FeCl$_3$·6H$_2$O and 5 mmol Na$_2$WO$_4$·2H$_2$O respectively into 25 ml distilled water. Then, adding a certain amount of ascorbic acid into FeCl$_3$ solution under continuous stirring for complete dissolution. Next, slowly adding Na$_2$WO$_4$ solution into the above mixture. After further stirring for 30 min, adding the mixture into a 100 mL autoclave, and maintaining it at 180° C. for 12 h. Then naturally cooling down the autoclave to room temperature. Collecting a resulting precipitate by centrifugation, and washing with distilled water and anhydrous ethanol several times, and drying in air at 80° C. for 6 h.

Figure 17:
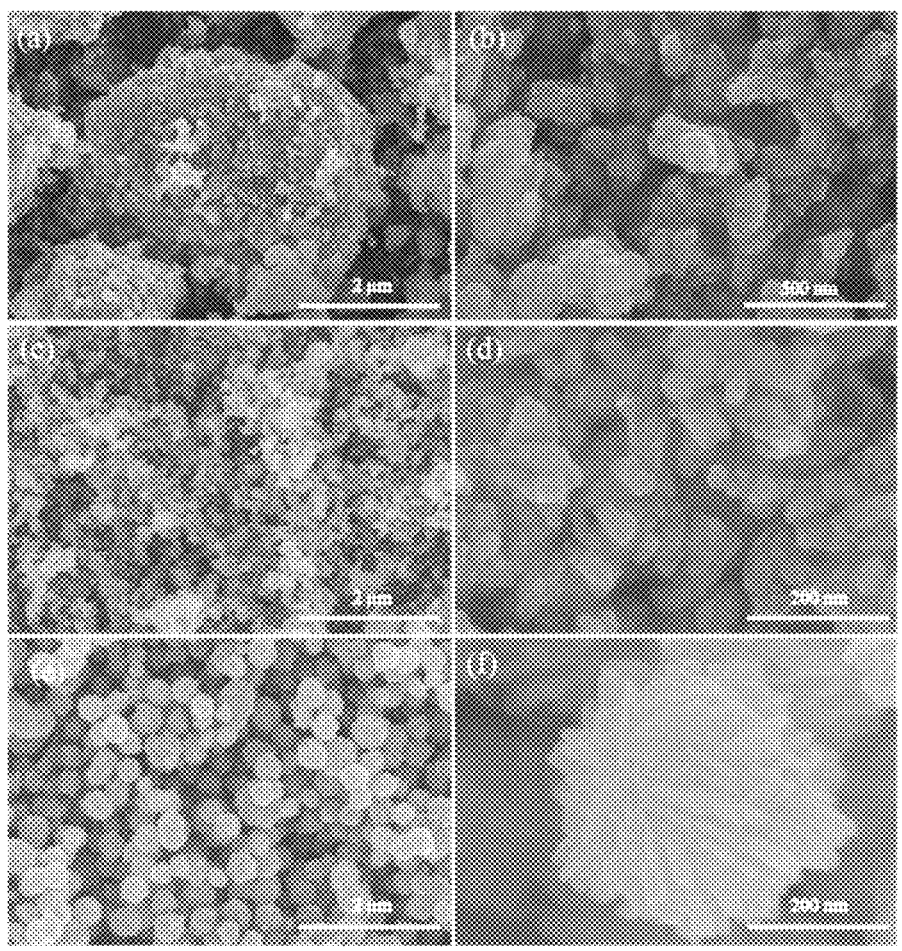
FIG. 17 illustrates SEM images of $FeWO_4$ generated under different ascorbic acid dosage conditions, wherein: molar ratios of $Fe^{3+}$: ascorbic acid are different, wherein, (a, b) 5:0.2, (c, d) 5:0.3, and (e, f) 5:1.

The effect of different amounts of ascorbic acid on the morphology of the product was studied and the studied results are shown in FIG. 17. FIG. 17 shows SEM images of the samples prepared in a case where different amounts of ascorbic acid (0.2 to 1 mmol) are present in the reaction system. When 0.2 mmol of ascorbic acid was added, disordered tiny particles were the main products ((a) (b) in FIG. 17). After increasing the amount of ascorbic acid (0.3 mmol), some particle aggregates were formed ((c) (d) in FIG. 17). Further increasing the amount of ascorbic acid to 0.5 mmol, the prepared samples consisted of snowflakes with perfect homogeneity and monodispersity ((a) (b) in FIG. 11). When the amount of ascorbic acid was up to 1 mmol, the product showed a spherical shape and consisted of nanorods ((e) (f) in FIG. 17). Thus, the successful preparation of novel FeWO4 nanostructures suggests that ascorbic acid can be used in this system not only as a reducing agent but also as a structure-directing agent to synthesize FeWO$_4$ products.

Effect of Different Raw Materials on FeWO$_4$

In case where step (1) of embodiment 2 does not change, respectively, A only replacing FeCl$_3$·6H$_2$O with equimolar Fe(NO$_3$)$_3$·9H$_2$O, and Bonly adding 0.1 mmol of cetyltrimethylammonium bromide when adding ascorbic acid.

Figure 18:
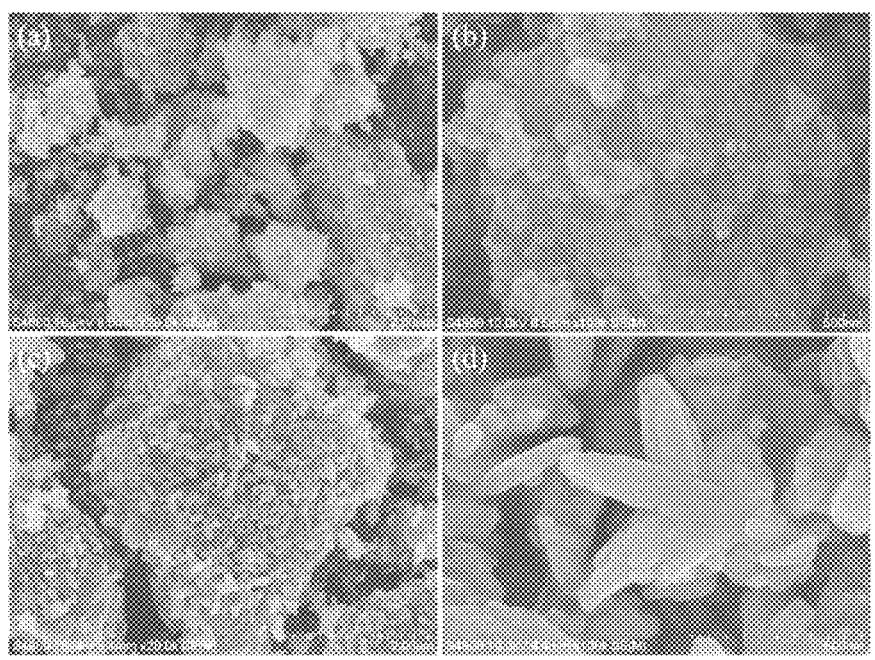
FIG. 18 illustrates SEM images of FeWO4 prepared from different raw materials, wherein, (a, b) $Fe(NO_3)_3$ was used instead of FeCl3; (c, d) 5 mmol $FeCl_3·6H_2O$, 5 mmol $Na_2WO_4·2H_2O$, 0.5 mmol ascorbic acid and 0.1 mmol of cetyltrimethylammonium bromide.

The results are shown in FIG. 18, wherein the morphology and size of the FeWO$_4$ products depend on the iron precursor salt used. The anion of the iron precursor salt determines the final structure of FeWO$_4$. Under similar conditions, a uniform snowflake-like structure assembled from nanorods could not be obtained by only using Fe(NO$_3$)$_3$ instead of FeCl$_3$. The corresponding SEM is shown in FIG. 18 (a) (b). In addition to the iron precursor salt, we found that the presence of CTAB also affects the morphology of the final product, as shown in FIG. 18 (c) (d). In case that CTAB exists, the final product can also consist of nanorods, but the snowflake-like organized structure would not exist at all. Thus, CTAB can further provide additional control over the morphology of the product.

Aflatoxin (AFB1) degradation experiments were performed as following steps of:

Coating 500 mg of flower-like FeWO$_4$-rGO composite material prepared in embodiment 2 on a glass substrate, and then adding it into 100 mL of corn oil (concentration 16.8 ppb) containing AFB1 with 500 rpm magnetic stirring. And then placing it in the dark and stirring it for 30 min, so as to achieve adsorption-desorption equilibrium. Using a 300 W xenon lamp to irradiate the suspension. Collecting 5 mL of corn oil at 0 min, 15 min, 30 min, 45 min, 60 min, and 75 min of irradiation time, respectively. The concentration of AFB1 in peanut oil was tested by liquid chromatography, and the results are shown in Table 1. The control groups were snowflake-like FeWO$_4$ and FeWO$_4$-rGO-U prepared as comparison examples.

TABLE 1

| Light time (min) | 0 | 15 | 30 | 45 | 60 | 75 |
|---|---|---|---|---|---|---|
| AFB$_1$concentration (ppb) in snowflake-like FeWO4group | 16.8 | 15.3 | 14.2 | 13.6 | 12.8 | 13.8 |
| AFB$_1$concentration (ppb) in snowflake-like FeWO4-rGO-Ugroup | 16.8 | 14.6 | 11.2 | 9.6 | 8.7 | 6.2 |
| AFB$_1$concentration (ppb) in snowflake-like FeWO4-rGOgroup | 16.8 | 12.1 | 9.6 | 4.1 | 3.6 | 2.5 |

It can be seen from Table 1, in comparison with snowflake-like FeWO$_4$ and FeWO$_4$-rGO-U, flower-like FeWO$_4$-rGO has excellent photocatalytic degradation performance for corn oil AFB$_1$.

Application Example 2

*Escherichia coli* bacterial fluids were mixed with the prepared materials, and irradiated with an optical cut-off filter ($\lambda$>420 nm) using a 300 W xenon lamp for antimicrobial performance evaluation experiments. The bacterial suspensions with different irradiation time intervals (0 min, 5 min, 10 min, 15 min, 20 min, 25 min) were taken and coated on LB agar plates, and incubated for 4 h at 37° C. in a thermostat to observe the growth of the colonies. At the same time, the bacterial fluids were diluted, and plate counting was performed, so as to determine the number of surviving bacteria and calculate the bactericidal efficiency.

$$\text{Bactericidal efficiency (\%)} = (N_0 - N_t)/N_0 \times 100\%$$

Note: $N_0$ and $N_t$ in the formula are the number of colonies counted in the control group and the sample plate respectively.

The experiment results are shown in Table 2.

TABLE 2

| Light time (min) | 0 | 5 | 10 | 15 | 20 | 25 |
|---|---|---|---|---|---|---|
| Bactericidal efficiency of snowflake-like FeWO$_4$ group | 1 | 0.91 | 0.83 | 0.79 | 0.75 | 0.71 |
| Bactericidal efficiency of snowflake-like FeWO$_4$-rGO-U group | 1 | 0.84 | 0.71 | 0.63 | 0.59 | 0.52 |
| Bactericidal efficiency of snowflake-like FeWO$_4$-rGO group | 1 | 0.65 | 0.42 | 0.36 | 0.21 | 0.08 |

As can be seen from Table 2, compared with snowflake-like FeWO$_4$ and FeWO$_4$-rGO-U, snowflake-like FeWO$_4$-rGO prepared in the present disclosure has excellent photocatalytic killing performance against *Escherichia coli*.

The foregoing is only a preferred embodiment of the present disclosure, and is not intended to be a limitation of the present disclosure in any other form, and any skilled person familiar with the art may use the technical content disclosed above to change or reformat into equivalent embodiments of equivalent changes. However, any simple modification, equivalent change or transformation of the above embodiments based on the technical substance of the present disclosure without departing from the content of the technical solutions of the present disclosure still belongs to the protection scope of the technical solutions of the present disclosure.

What is claimed is:

1. A radiant catalytic ionization detoxification system, comprising an air-liquid mixer (1) configured to mix air carrying radiant catalytic ionized Reactive Oxygen Species with liquid material to be detoxified, and a reaction tube (4) configured to circulate the mixed air-liquid mixture;
   wherein the reaction tube (1) comprises a plurality of U-shaped tubes (4-1), and a connecting tube (4-2) configured to connect the plurality of U-shaped tubes (4-1); an air supplement tube (4-3) is detachably connected at a distal end of a straight tube section of the plurality of U-shaped tubes (4-1), the air supplement tube (4-3) being configured to introduce the air carrying radiant catalytic ionized Reactive Oxygen Species into the plurality of U-shaped tubes (4-1);
   wherein a plurality of air supplement holes (4-31) are disposed on a wall of the air supplement tube (4-3);
   wherein a plurality of fins (4-32) are disposed on the air supplement tube (4-3);
   wherein the air carrying radiant catalytic ionized Reactive Oxygen Species are provided by a radiant catalytic ionization chamber (2); the radiant catalytic ionization chamber (2) comprises a chamber body (2-1), a plurality of mesh panels (2-2) disposed in the chamber body (2-1) and a lamp tube (2-3) configured to provide a radiant light source;
   wherein a photocatalytic material which produces Reactive Oxygen Species upon light irradiation is coated on the plurality of mesh panels (2-2);
   wherein a fixing frame (2-4) is further disposed in the chamber body (2-1), the fixing frame (2-4) being configured to fix the plurality of mesh panels (2-2) and the lamp tube (2-3);
   wherein a fixing hole (2-41) configured to fix the lamp tube (2-3) and a fixing rod (2-42) configured to fix the plurality of mesh panels (2-2) are disposed on the fixing frame (2-4);
   wherein a mounting hole (2-21) configured to be passed through by the lamp tube (2-3) and a fixing hole (2-22) configured to be passed through by the fixing rod (2-42) are disposed on the plurality of mesh panels (2-2); and
   wherein the photocatalytic material is $FeWO_4$-rGO composite material.

2. A radiant catalytic ionization detoxification method, comprising:
   providing the radiant catalytic ionization detoxification system according to claim 1,
   generating Reactive Oxygen Species according to radiant catalytic ionization,
   mixing air carrying radiant catalytic ionized Reactive Oxygen Species with liquid materials to be detoxified, and
   detoxifying bacteria or aflatoxin in the liquid materials with the Reactive Oxygen Species.

* * * * *